(12) United States Patent
Demuth et al.

(10) Patent No.: US 6,586,645 B2
(45) Date of Patent: Jul. 1, 2003

(54) CONTINUOUS ADIABATIC PROCESS FOR PREPARING NITROCHLOROBENZENE

(75) Inventors: Ralf Demuth, Hilden (DE); Bernd-Michael König, Bergisch Gladbach (DE); Thomas Linn, Grevenbroich (DE); Hans-Joachim Raatz, Leverkusen (DE); Hans-Martin Weber, Leverkusen (DE); Eberhard Zirngiebl, Köln (DE); Ricarda Leiberich, Langen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/078,655

(22) Filed: Feb. 19, 2002

(65) Prior Publication Data

US 2002/0161269 A1 Oct. 31, 2002

(30) Foreign Application Priority Data

Feb. 23, 2001 (DE) ......................................... 101 08 979

(51) Int. Cl.$^7$ ................................................ C07C 205/00
(52) U.S. Cl. ........................................ 568/937; 568/936
(58) Field of Search .................................. 568/936, 937

(56) References Cited

U.S. PATENT DOCUMENTS

| | | | | |
|---|---|---|---|---|
| 4,021,498 | A | 5/1977 | Alexanderson et al. | 260/645 |
| 4,453,027 | A | 6/1984 | Vaidyanathan | 568/937 |
| 4,772,757 | A | 9/1988 | Lailach et al. | 568/939 |
| 5,714,647 | A | 2/1998 | Blank et al. | 568/937 |
| 5,763,687 | A | 6/1998 | Morisaki et al. | 568/927 |
| 6,242,657 | B1 * | 6/2001 | Konig et al. | 568/936 |

* cited by examiner

*Primary Examiner*—J. Parsa
(74) *Attorney, Agent, or Firm*—Godfried R. Akorli; Diderico van Eyl

(57) ABSTRACT

The present invention relates to a continuous adiabatic process for preparing nitrochlorobenzene, in which the waste sulfuric acid produced during the practice of the process is reconcentrated and recycled into the nitration reaction.

10 Claims, No Drawings

CONTINUOUS ADIABATIC PROCESS FOR PREPARING NITROCHLOROBENZENE

BACKGROUND OF THE INVENTION

The present invention relates to a continuous adiabatic process for preparing nitrochlorobenzene, in which the waste sulfuric acid produced during the practice of the process is reconcentrated and recycled into the nitration reaction.

Nitrochlorobenzenes are important intermediates in the preparation of dyes, pharmaceutics, and pesticides. There is a particularly high demand for ortho-nitrochlorobenzene, which is obtained in the nitration of chlorobenzene to about 35%. Para-nitrochlorobenzene, too, has a number of industrial uses. Substantially undesired is the production of meta-nitrochlorobenzene, which has only very limited industrial applications.

Industrially, nitrochlorobenzenes are prepared by nitration of chlorobenzene. For nitration, it is customary to use a mixture of sulfuric acid, nitric acid, and water. During the reaction, a significant amount of waste sulfuric acid contaminated with organic compounds is produced, requiring complicated and expensive work-up. To avoid the production of waste acid, processes comprising reconcentration of the sulfuric acid, in which most of the water and the organic compounds are removed from the sulfuric acid, which is then recirculated into the nitration reaction, have been developed. The reconcentration of the waste sulfuric acid succeeds in a particularly elegant manner when the nitration reaction is carried out under adiabatic conditions, since in this case there is no heat exchange with the environment and the energy released during the process can be used to reconcentrate the waste sulfuric acid. Moreover, in contrast to an isothermal process with dissipation of heat, it is possible to use materials of a better quality, which, under the reaction conditions, show considerably few signs of corrosion.

U.S. Pat. No. 4,453,027 claims an adiabatic nitration process for the preparation of mononitrohalogenobenzenes. The nitrating acid used contains 11.1% by weight of nitric acid, 68.5% by weight of sulfuric acid, and 20.4% of water. The temperature of the resulting waste sulfuric acid after the reaction is stated to be from 100 to 110° C. If the reaction is carried out adiabatically, at the nitric acid concentration mentioned above, the temperature increase during the reaction is about 100° C., so that the reaction must be started at from 0 to 10° C. and the reactants to be fed in must be available at this temperature. If 60% strength nitric acid is used, the resulting waste sulfuric acid is reconcentrated to 84.1%; if 98% strength nitric acid is used, this value is still 77.3% by weight. If the heat of the reaction is used for the reconcentration, the waste sulfuric acid cools to about 0° C. From a technical and an economical point of view, such a process no longer makes sense, since it requires the use of refrigerating brines and special apparatus.

U.S. Pat. No. 4,021,498 describes the adiabatic mononitration of aromatic compounds. It is emphasized that the reaction must be carried out with vigorous stirring to achieve complete conversion. Even in a tube reactor, a stirrer is required. However, it is not stated how vigorous the stirring must be to achieve complete conversion. This patent focuses on the adiabatic mononitration of benzene, since all examples refer to this reaction. Details of the adiabatic mononitration of halogenated aromatic compounds in general and chlorobenzene in particular are not given.

EP 779,270 A describes a process for preparing mononitroaromatic compounds using reactors having a large number of special internals that are arranged in such a manner that adjacent internals are located virtually perpendicular to each other. This process has the disadvantage that it requires the use of reactors designed especially for this process, the purchase of these reactors being a costly investment.

EP 675,104 A describes an adiabatic process for nitrating halogenobenzenes in which the reactants are mixed while applying a certain mixing energy, mixing being carried out in a temperature range of from 60 to 160° C. Using the temperatures mentioned, it is possible to obtain the high reaction rate required for adiabatic operation. However, this process has the disadvantage that relatively high amounts of undesirable meta-nitrochlorobenzene are obtained, the removal of which is complicated and costly.

Accordingly, there was a need for a process for the continuous preparation of nitrochlorobenzene, which process is carried out under adiabatic conditions and at the same time affords relatively low amounts of meta-nitrochlorobenzene.

SUMMARY OF THE INVENTION

Surprisingly, we have found a process for the continuous preparation of nitrochlorobenzene comprising reacting chlorobenzene with sulfuric acid, nitric acid, and water, wherein (a) the feedstocks chlorobenzene, sulfuric acid, nitric acid, and water are introduced simultaneously or successively into a reactor equipped with mixing elements and are mixed at an average mixing power density of 1.5 to 40 watt/liter and at a reaction mixture temperature during initial mixing of 10 to 50° C., (b) the content of sulfuric acid in the reaction mixture during mixing, based on the sum of sulfuric acid, nitric acid, and water, is 70 to 80% by weight, (c) the reaction proceeds under adiabatic conditions, (d) at the reactor outlet, the crude nitrochlorobenzene is separated from the waste sulfuric acid, and (e) the waste sulfuric acid is reconcentrated to the original content of sulfuric acid and recycled into the nitration reaction.

DETAILED DESCRIPTION OF THE INVENTION

The feedstocks used in the process according to the invention are chlorobenzene, sulfuric acid, nitric acid and water, where the chlorobenzene may contain nitrochlorobenzene. The amount of nitrochlorobenzene is generally 0 to 20% by weight. Here, water can be used as such or else introduced into the reaction as dilution water of the nitric acid and/or the sulfuric acid. Preferably, water is introduced into the reaction as dilution water of the nitric acid and/or the sulfuric acid.

In the process according to the invention, the feedstocks chloro-benzene, sulfuric acid, nitric acid, and water are introduced individually or as mixtures into a reactor equipped with mixing elements. The feedstocks can be introduced into the reactor simultaneously or successively. Introduction into the reactor can be carried out, for example, by adding chlorobenzene and nitric acid and, if appropriate, water as separate strains simultaneously or successively to the reconcentrated recycled sulfuric acid, it being possible for the nitric acid to be diluted by water and/or sulfuric acid. It is also possible to pre-mix chlorobenzene with water and sulfuric acid and to introduce the resulting mixture as a separate stream into the reactor. In the reactor, mixing with nitric acid, which may be mixed with sulfuric acid and/or water, takes place. It is furthermore possible to introduce chlorobenzene and a nitrating acid prepared by mixing sulfuric acid, nitric acid, and water in separate streams into the reactor. In a preferred embodiment of the process according to the invention, nitric acid and reconcentrated recycled sulfuric acid are mixed to give a nitrating acid, and nitrating acid and chlorobenzene are introduced into the reactor in separate streams. For the reaction to succeed, it is of minor importance in which order and composition the reactants are introduced into the reactor, as long as the reaction mixture obtained once all reactants have been mixed has the composition according to the invention and mixing takes place at the intensity according to the invention and at the temperature according to the invention.

At the time of mixing, the content of sulfuric acid in the reaction mixture, based on the sum of sulfuric acid, nitric acid, and water, is 56.5 to 84.5% by weight, preferably 67.1 to 80.9% by weight, particularly preferably 69.5 to 78.6% by weight.

The content of nitric acid at the time of mixing, based on the sum of nitric acid, sulfuric acid, and water, is 3 to 10% by weight, preferably 4 to 8% by weight, particularly preferably 4 to 6% by weight. Nitric acid can be employed in highly concentrated form or in the form of azeotropic nitric acid, for example, with a content of 60 to 98% by weight of nitric acid, but is preferably used in the form of dilute nitric acid of about 60 to 70% by weight, which can be obtained at low cost.

In the process according to the invention, all reactants are mixed such that the average mixing power density in the reactor is 1.5 to 40 watt/liter, preferably 1.5 to 30 watt/liter. For mixing, it is possible to use the mixing elements known in the art, for example, static mixers, pumps, nozzles, stirrers, or combinations thereof. The mixing power density, expressed in watt per liter, in a continuously operated reactor is determined as follows:

Mixing power density=power $P$/volume $V$ [W/l]

$P$=Throughput of reactants [$m^3/s$]×dynamic pressure drop $\Delta p_{dyn}$ [$N/m^2$]

$\Delta p_{dyn}$=total pressure drop $\Delta p_{total}$-static pressure drop $\Delta p_{stat}$ Since the average mixing power density acts on each liter of the reaction mixture and this reaction mixture is present only in the reactor, the volume of the reactor in which the reaction is carried out is used as volume V when calculating the average mixing power density.

During initial mixing, the temperature of the reaction mixture is 10 to 50° C., preferably 20 to 50° C. and particularly preferably 30 to 45° C. Depending on the temperature of the reaction mixture during mixing and on the conversion, the final temperature generally does not exceed 130° C. and is preferably below 100° C.

The reaction should preferably proceed without any backmixing, which can be achieved, for example, by dispersing the reaction mixture. This is preferably carried out by internals or elements provided in the reactor for this purpose, such as, for example, perforated metal sheets, slotted metal sheets, impact baffles, veins, baffle plates, static mixers, or stirrers.

Continuously operated reactors suitable for the process according to the invention that may be mentioned are, for example, tubular reactors, preferably having internals for dispersing, such as, for example, perforated metal sheets, slotted metal sheets, impact baffles, veins, and baffle plates, static mixers, stirrers and the like, vigorously agitated kettles in cascade arrangement, loop reactors having the internals described above, combinations of a plurality of the apparatuses mentioned, and further reactors acting in the same manner, such as chamber reactors having stirrers in each chamber. In the process according to the invention, preference is given to using tubular reactors having internals. Preferred internals are perforated metal sheets. All internals represent subdivisions of the entire apparatus that equally serve for dispersion and the substantial prevention of backmixing.

After the intensive mixing, after each dispersion, or after the mixture has flowed through a certain part-length of the reactor, coalescence of the dispersion droplets is observed, which can be reversed by redispersion. The number of redispersion operations is preferably 2 to 50, with preference 3 to 30, particularly preferably 4 to 20. The average mixing power density according to the invention of 1.5 to 40 watt/liter, which during mixing of the reactants acts on each liter of the reaction mixture, is preferably used to overcome the pressure drops occurring during the dispersion operations.

According to the equation of the process according to the invention, chlorobenzene is reacted with nitric acid to give nitrochlorobenzene and water. Thus, chlorobenzene and nitric acid are introduced into the process, and nitrochlorobenzene and water are discharged, the sulfuric acid/water mixture described being the reaction medium. Since, in the case of industrial implementation, it is advantageous to use dilute nitric acids, the dilution water of the nitric acid must be discharged in addition to the water of the reaction.

In the process according to the invention, the crude nitrochlorobenzene is separated from the waste sulfuric acid at the reactor outlet. The separation can be carried out in apparatus known to persons skilled in the art or with the aid of means known to persons skilled in the art. Thus, separation may be effected, for example, using a static separator. The resulting waste sulfuric acid is substantially free of nitric acid and contains mainly sulfuric acid and water and possibly small amounts of organic impurities and/or nitrosylsulfuric acid. According to the invention, the sulfuric acid concentration of the waste sulfuric acid is 70 to 85% by weight, preferably 72 to 80% by weight, particularly preferably 76 to 79% by weight.

For re-use, the waste sulfuric acid is, according to the invention, reconcentrated to the original sulfuric acid content and recycled into the nitration reaction. During reconcentration, water (i.e., water of the reaction and, if appropriate, dilution water) is removed by distillation. To this end, use is preferably made of the heat of the reaction taken up by the waste sulfuric acid.

The reconcentration is preferably carried out in an evaporator that is preferably operated at a pressure of 60 to 200 mbar, particularly preferably 60 to 180 mbar, and very particularly preferably 80 to 150 mbar. Here, the temperature of the waste sulfuric acid in the evaporator outlet is preferably 100 to 200° C., particularly preferably 130 to 190° C., and very particularly preferably 145 to 165° C. The temperature of the reconcentrated waste sulfuric acid that is discharged is preferably used to heat the waste sulfuric acid flowing into the evaporator in a countercurrent heat exchanger.

The reconcentration is preferably carried out in a one-step process, using, preferably, a commercial cascade evaporator with tantalum tube bundle in which, from the point of entry, the acid concentration is increased with each cascade, so that an acid having a relatively low concentration is present in the first cascades. It is an advantage of the low concentration of the first cascade that, first, the boiling point is still low, resulting in a high driving temperature distance for the heat transfer (small evaporator), and, second, that at low acid concentrations it is easier to remove any nitrosylsulfuric acid present in the waste acid from the reaction. Thus, by using a cascade evaporator in the process according to the invention, it is possible to avoid the blowing out of nitrosylsulfuric acid with sulfur dioxide, which is usually carried out, and thus means an additional process step. To prevent the formation of deposits of organic compounds, particularly nitrochlorobenzene, on the condenser, the condenser is, in a preferred embodiment, continuously sprinkled with chlorobenzene. The organic phase that is being discharged and comprises chlorobenzene and nitrochlorobenzene can be used as feedstock for the process according to the invention.

The following examples further illustrate details for the process of this invention. The invention, which is set forth in the foregoing disclosure, is not to be limited either in spirit or scope by these examples. Those skilled in the art will readily understand that known variations of the conditions of the following procedures can be used.

EXAMPLES

Example 1

186 kg/h of 81% strength sulfuric acid, 13.3 kg/h of 70.6% strength nitric acid, and 19.7 kg/h of chlorobenzene, which contained about 7 to 8% nitrochlorobenzene, were introduced continuously into a tubular reactor. The average mixing power density was 6.2 watt/l. The temperature during mixing was 40° C. After about 180 sec the reaction mixture had reached the end of the reactor; the temperature at the reactor outlet was 92–94° C. The reaction mixture was heated to about 120° C., and phase separation occurred within 90 seconds in a static separator. The waste sulfuric acid was reconcentrated to the original sulfuric acid content and recycled into the nitration reaction. The condenser used for condensing the water was sprinkled with chlorobenzene to prevent the formation of deposits of any nitrochlorobenzene dissolved in the waste sulfuric acid. The crude nitrochlorobenzene phase was analyzed by gas chromatography and had the following composition:

| | |
|---|---|
| Chlorobenzene: | 8.97% |
| ortho-Nitrochlorobenzene: | 34.14% |
| meta-Nitrochlorobenzene: | 0.87% |
| para-Nitrochlorobenzene: | 55.83% |
| Dinitro compounds: | 0.19% |

Example 2 (Not According to the Invention)

186 kg/h of 75% strength sulfuric acid, 9.6 kg/h of 65% strength nitric acid, and 12.3 kg/h of chlorobenzene, which contained about 7% nitrochlorobenzene, were introduced continuously into a tubular reactor. The average mixing power density was 6.2 watt/l. The temperature during mixing was about 110° C. After about 180 sec the reaction mixture had reached the end of the reactor; the temperature at the reactor outlet was 140° C. Phase separation occurred in a static separator. The waste sulfuric acid was reconcentrated to the original sulfuric acid content and recycled into the nitration reaction. The condenser used for condensing the water was sprinkled with chlorobenzene to prevent the formation of deposits of any nitrochlorobenzene dissolved in the waste sulfuric acid. The crude nitrochlorobenzene phase was analyzed by gas chromatography and had the following composition:

| | |
|---|---|
| Chlorobenzene: | 2.70% |
| ortho-Nitrochlorobenzene: | 37.61% |
| meta-Nitrochlorobenzene: | 1.56% |
| para-Nitrochlorobenzene: | 57.83% |
| Dinitro compounds: | 0.26% |

What is claimed is:

1. A process for the continuous preparation of nitrochlorobenzene comprising reacting chlorobenzene with sulfuric acid, nitric acid, and water, wherein (a) the feedstocks chlorobenzene, sulfuric acid, nitric acid, and water are introduced simultaneously or successively into a reactor equipped with mixing elements and are mixed at an average mixing power density of 1.5 to 40 watt/liter and at a reaction mixture temperature during initial mixing of 10 to 50° C., (b) the content of sulfuric acid in the reaction mixture during mixing, based on the sum of sulfuric acid, nitric acid, and water, is 70 to 80% by weight, (c) the reaction proceeds under adiabatic conditions, (d) at the reactor outlet, the crude nitrochlorobenzene is separated from the waste sulfuric acid, and (e) the waste sulfuric acid is reconcentrated to the original content of sulfuric acid and recycled into the nitration reaction.

2. A process according to claim 1 wherein the content of nitric acid in the reaction mixture during mixing, based on the sum of sulfuric acid, nitric acid, and water, is 3 to 10% by weight.

3. A process according to claim 1 wherein the nitric acid is employed in the form of a 60 to 70% strength nitric acid.

4. A process according to claim 1 wherein 1 to 1.3 equivalents of chlorobenzene is employed per equivalent of nitric acid.

5. A process according to claim 1 wherein the average mixing power density is 1.5 to 30 watt/liter.

6. A process according to claim 1 wherein the temperature of the reaction mixture during initial mixing is 20 to 50° C.

7. A process according to claim 1 wherein the reconcentration of the waste sulfuric acid is carried out in an evaporator.

8. A process according to claim 1 wherein the reconcentration of the waste sulfuric acid is carried out in an evaporator at a pressure of 60 to 200 mbar.

9. A process according to claim 7 wherein the temperature of the waste sulfuric acid in the evaporator outlet is 100 to 200° C.

10. A process according to claim 7 wherein the evaporator is a cascade evaporator with tantalum tube bundle.

* * * * *